United States Patent [19]

Paslean et al.

[11] Patent Number: 4,673,762

[45] Date of Patent: Jun. 16, 1987

[54] DECOLORIZING ETHANOLAMINES WITH ALKYLENE OXIDES

[75] Inventors: James H. Paslean, Port Neches; Charles S. Steele, Nederland, both of Tex.

[73] Assignee: Texaco Inc., White Plains, N.Y.

[21] Appl. No.: 866,676

[22] Filed: May 27, 1986

[51] Int. Cl.[4] ............................................. C07C 85/26
[52] U.S. Cl. .................................................... 564/497
[58] Field of Search ......................................... 564/497

[56] References Cited

U.S. PATENT DOCUMENTS

| | | | |
|---|---|---|---|
| 2,716,136 | 8/1955 | Paulsen | 564/497 |
| 3,207,790 | 9/1965 | Glew et al. | 564/497 |
| 3,428,684 | 2/1969 | Tindall | 564/497 |
| 3,453,183 | 7/1969 | Okubo et al. | 564/497 X |
| 3,819,710 | 6/1974 | Jordan | 564/497 |
| 4,507,475 | 3/1985 | Straehle | 564/497 X |

*Primary Examiner*—Paul F. Shaver
*Attorney, Agent, or Firm*—Jack H. Park; Kenneth R. Priem; Richard A. Morgan

[57] ABSTRACT

It has been found that a small amount of alkylene oxide prevents Pt-Co color buildup in mono, di and triethanolamine. Alkylene oxide also reduces undesirable blue, aqua or straw hues which may develop.

3 Claims, No Drawings

DECOLORIZING ETHANOLAMINES WITH ALKYLENE OXIDES

BACKGROUND OF THE INVENTION

1. Field of the Invention

The invention is a method of decolorizing or stabilizing triethanolamine, diethanolamine or monoethanolamine by treatment with an alkylene oxide.

2. Description of Other Related Methods in the Field

Many decolorizing agents now in use remove color by physical adsorption. The most common materials to remove color by this means are represented by charcoals, blacks (such as carbon black), clays and earths. Other compounds remove color by chemical reaction and are frequently more specific as to the materials they can remove color from than the physical adsorption agents. While attempts have been made to predict compound colors, such as by electronegative or steric contributions of substituents to aromatic rings, numerous exceptions to rules relating color to structure require color prediction to be based largely on empirical observations, see Griffiths, John; *Colour and Constitution of Organic Molecules;* London: Academic Press (1976), pp. 89–90. As a result, attempts to remove color from a specific compound tend to be strictly trial and error operations.

Specific examples may be seen in the decolorization of diethanolamine and triethanolamine. U.S. Pat. No. 3,207,790 describes the decolorization of triethanolamine through the use of sodium or potassium borohydride. U.S. Pat. No. 3,207,790 and 3,159,276 discuss decolorizing ethanolamines with borohydride. Amines may also be decolorized by the use of calcium hydroxide according to U.S. Pat. No. 2,716,136 or with hydrazine in U.S. Pat. No. 2,901,513.

SUMMARY OF THE INVENTION

The invention is a method for decolorizing and/or stabilizing monoethanolamine, diethanolamine and triethanolamine by adding a small amount of ethylene oxide, propylene oxide or mixtures thereof.

DESCRIPTION OF THE PREFERRED EMBODIMENTS

Monoethanolamine, diethanolamine and triethanolamine are typically prepared by reaction of ammonia with ethylene oxide. The recovered products are water white or nearly water white as measured by Pt-Co color of zero on a scale of zero to approximately one thousand. However on standing, the Pt-Co color increases and over a period of time an undesirable blue, aqua or straw hue in triethanolamine or straw hue in diethanolamine may also develop. This darkening occurs regardless of whether or not the amine is exposed to sunlight or air. The darkening is objectionable in many instances and can, depending on the end use, make the amine unusable. Triethanolamine, for example, is used in cosmetics and must be color-free to be commercially acceptable.

It has been found according to the present invention that the color of ethanolamines is substantially reduced by adding an amount of ethylene oxide or propylene oxide sufficient to remove the color. It is preferred that the alkylene oxide be added in an amount of 50 to 3000 ppm. by weight. However, it is understood that the amount added is dependent upon the extent of coloration, and therefore in the broadest aspect of the invention, sufficient alkylene oxide must be added to effect substantial color reduction, whatever its extent.

It has also been found that the color of monoethanolamine, diethanolamine or triethanolamine is stabilized by adding typically 50 to 3000 ppm by weight alkylene oxide. This prevents the formation of undesirable hues when added in an effective amount which may be determined by routine analysis to either conserve alkylene oxide or increase protection.

This addition is accomplished efficiently by simple addition of alkylene oxide to the amine. The two liquids have appreciable solubility and the alkylene oxide is easily dissolved in the amine by gentle stirring for a short period of time.

The present method may be used in a continuous process, integral to the amine manufacturing process. Applicants have practiced the invention in a batch process wherein alkylene oxide was added to freshly made, clear and water white amine. This prevented the formation of color bodies. The product was then stored without concern for straw or other off color hues developing upon storage.

It appears that alkylene oxide displays an unexplained superior compatibility in decolorizing these three amines. This superior compatibility is demonstrated in the following examples:

EXAMPLE I

Separate triethanolamine samples were mixed with ethylene oxide and potassium borohydride and stored in the laboratory at room temperature and at 120° F. After 69 days the color was measured by ASTM D-1209-69 (1974). Samples analyzed are reported in the table below:

| Treatment | Temperature | Color, Pt—Co |
| --- | --- | --- |
| None | Room | 30, light aqua hue |
| Potassium borohydride, 50 ppm | Room | 30 |
| Ethylene oxide, 530 ppm | Room | 15 |
| Ethylene oxide, 2600 ppm | Room | 10 |
| None | 120° F. | 35, light aqua hue |
| Potassium borohydride, 60 ppm | 120° F. | 35 |
| Ethylene oxide, 1000 ppm | 120° F. | 15 |

EXAMPLE II

A. Separate identical samples of low color triethanolamine (0 Pt-Co color) were treated with 250 ppm of ethylene oxide or 250 ppm of propylene oxide and stored with an untreated triethanolamine sample at room temperature for 68 days. The control sample increased to 10 Pt-Co color while the treated samples had 0 Pt-Co and 5 Pt-Co colors, respectively.

B. The test was repeated with samples of low color triethanolamine at 120° F. The untreated sample increased in color from 0 Pt-Co to 35 Pt-Co color after 64 days. The treated samples had lower colors as shown in the following table.

| Additive, ppm | Color, Pt—Co |
| --- | --- |
| Ethylene oxide, 250 | 10 |
| Propylene oxide, 250 | 10 |
| Ethylene oxide, 1000 | 5 |

C. A slightly higher colored triethanolamine was mixed with ethylene oxide and propylene oxide and stored at 120° F. while exposed to air. A second set was treated with the same alkylene oxides and stored at 120° F. under nitrogen. Lower colors were found on the samples containing the oxides as shown in the table below.

| Additive, ppm | Air/nitrogen pad | Color, Pt—Co |
| --- | --- | --- |
| None | Air | 35 |
| Ethylene oxide, 425 | Air | 5 |
| Ethylene oxide, 1000 | Air | 10 |
| Propylene oxide, 250 | Air | 10 |
| Propylene oxide, 1000 | Air | 10 |
| None | Nitrogen | 35 |
| Ethylene oxide, 1000 | Nitrogen | 5 |
| Propylene oxide, 1000 | Nitrogen | 10 |

EXAMPLE III

A sample of triethanolamine having a 20 Pt-Co color was treated with ethylene oxide and stored at room temperature and at 120° F. for 137 days. A like sample was treated with potassium borohydride and kept under the same conditions. Another sample containing no additives was stored under the same conditions. It increased to 30 Pt-Co color at room temperature and to 50 Pt-Co color at 120° F. The colors of the treated samples are listed in the table below.

| Additive, ppm | Temperature | Color, Pt—Co |
| --- | --- | --- |
| Ethylene oxide, 1000 | Room | 15 |
| Ethylene oxide, 1200 | 120° F. | 30 |
| Potassium borohydride, 56 | Room | 35 |
| Potassium borohydride, 54 | 120° F. | 40 |

EXAMPLE IV

Monoethanolamine has a 0 Pt-Co color during a typical production run. A 0 Pt-Co color sample was stored at 120° F. for 58 days under air pad. The sample tested 120 Pt-Co with an off hue. A second sample was mixed with 514 ppm ethylene oxide and stored under the same conditions. The treated sample tested 45 Pt-Co color after 58 days.

Many modifications may be made to the method of this invention without departing from the spirit and scope of the invention which is defined only in the appended claims.

What is claimed is:

1. A method for decolorizing monoethanolamine, diethanolamine or triethanolamine comprising:
    adding an alkylene oxide selected from the group consisting of ethylene oxide, propylene oxide and mixtures thereof.

2. The method of claim 1 wherein 50 to 3000 ppm alkylene oxide is added.

3. A method for preventing color buildup in monoethanolamine, diethanolamine or triethanolamine comprising adding 50 to 3000 ppm of an alkylene oxide selected from the group consisting of ethylene oxide, propylene oxide and mixtures thereof.

* * * * *